United States Patent
Appeldoorn

(10) Patent No.: US 10,015,997 B2
(45) Date of Patent: Jul. 10, 2018

(54) OSTOMY GARMENT

(71) Applicant: JOEIES, Chilliwack (CA)

(72) Inventor: Brandee Appeldoorn, New Westminster (CA)

(*) Notice: Subject to any disclaimer, the term of this patent is extended or adjusted under 35 U.S.C. 154(b) by 328 days.

(21) Appl. No.: 14/677,809

(22) Filed: Apr. 2, 2015

(65) Prior Publication Data
US 2015/0282541 A1 Oct. 8, 2015

Related U.S. Application Data

(60) Provisional application No. 61/974,830, filed on Apr. 3, 2014.

(51) Int. Cl.
| A61F 5/44 | (2006.01) |
| A41B 9/12 | (2006.01) |
| A41D 13/12 | (2006.01) |
| A61F 5/449 | (2006.01) |

(52) U.S. Cl.
CPC .......... *A41B 9/12* (2013.01); *A41D 13/1254* (2013.01); *A61F 5/449* (2013.01)

(58) Field of Classification Search
CPC ........ A61F 5/449; A41B 9/12; A41D 13/1254
See application file for complete search history.

(56) References Cited

U.S. PATENT DOCUMENTS

| 4,495,662 A | 1/1985 | Miller |
| 4,533,355 A | 8/1985 | Fair |
| 4,888,006 A | 12/1989 | Beaupeid |
| 5,626,570 A * | 5/1997 | Gallo ............... A61F 5/449 2/49.2 |
| 5,653,701 A | 8/1997 | Millman |
| 6,110,156 A * | 8/2000 | Mendonca ........... A61F 5/445 604/345 |
| 6,202,222 B1 * | 3/2001 | Robbins ............. A41B 9/001 2/400 |
| 6,328,721 B1 | 12/2001 | Prohaska |
| 6,468,254 B2 * | 10/2002 | Gupton ............ A41D 13/1254 604/345 |
| 7,313,832 B2 | 1/2008 | Worsoee |
| 7,650,702 B2 | 1/2010 | Jensen |
| 2006/0047256 A1 * | 3/2006 | Levesque ............ A61F 5/449 604/345 |

FOREIGN PATENT DOCUMENTS

EP 0661027 7/1995

* cited by examiner

*Primary Examiner* — Benjamin Klein

(57) ABSTRACT

A garment for accommodating an ostomy pouch, the garment comprising a pocket for containing the ostomy pouch, the pocket having a first opening towards a user of the garment when the garment is worn for inserting the ostomy pouch therethrough and into the pocket. The garment also comprises two or more bands encircling the garment, for exerting a compressive force against the user when the garment is worn. Furthermore, a mid-line along a length of the pocket intersects a mid-line of at least one of the two or more bands.

16 Claims, 4 Drawing Sheets

OSTOMY GARMENT

This application claims an invention which was disclosed in Provisional Application No. 61/974,830, filed Apr. 3, 2014, entitled "OSTOMY GARMENT". The benefit under 35 USC § 119(e) of the United States provisional application is hereby claimed, and the aforementioned application is hereby incorporated herein by reference.

FIELD

The present disclosure relates to an ostomy garment.

BACKGROUND

For individuals who have undergone "ostomy" procedures to have internal structures (such as portions of an intestinal tract and/or urinary tract) removed, an external opening (stoma) is often created to re-route bodily waste. The stoma is commonly created in the abdominal wall in these procedures, though the exact location may vary depending on the circumstances of the procedure. An ostomy pouch is coupled to the stoma to collect the waste.

Ostomy procedures and the subsequent formation of stomas are physically and psychologically intrusive. The patient's ability to engage in physical activity, and conceal the ostomy pouch while engaging in activity, is often impaired. Ostomy garments have been disclosed in the prior art (e.g. U.S. Pat. Nos. 6,202,222, 5,626,570, 4,495,662 and 7,313,832) that at least partially assist in concealing the ostomy pouch.

It would be beneficial to devise a garment for accommodating an ostomy pouch that allows an ostomate to accommodate the pouch in an aesthetically acceptable manner. In addition, it would be beneficial to devise a garment that allows an ostomate to engage in physical activity while comfortably carrying the ostomy pouch.

SUMMARY

According to an aspect the present disclosure provides a garment for accommodating an ostomy pouch having a flange, the garment comprising a pocket for containing the ostomy pouch, the pocket having a first opening that faces a user of the garment when the garment is worn, the first opening for inserting the ostomy pouch therethrough and into the pocket; and two or more bands encircling the garment for exerting a compressive force against the user when the garment is worn; wherein a mid-line along a length of the pocket intersects a mid-line of at least one of the two or more bands.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more exemplary embodiments.

DETAILED DESCRIPTION

Figure 1:
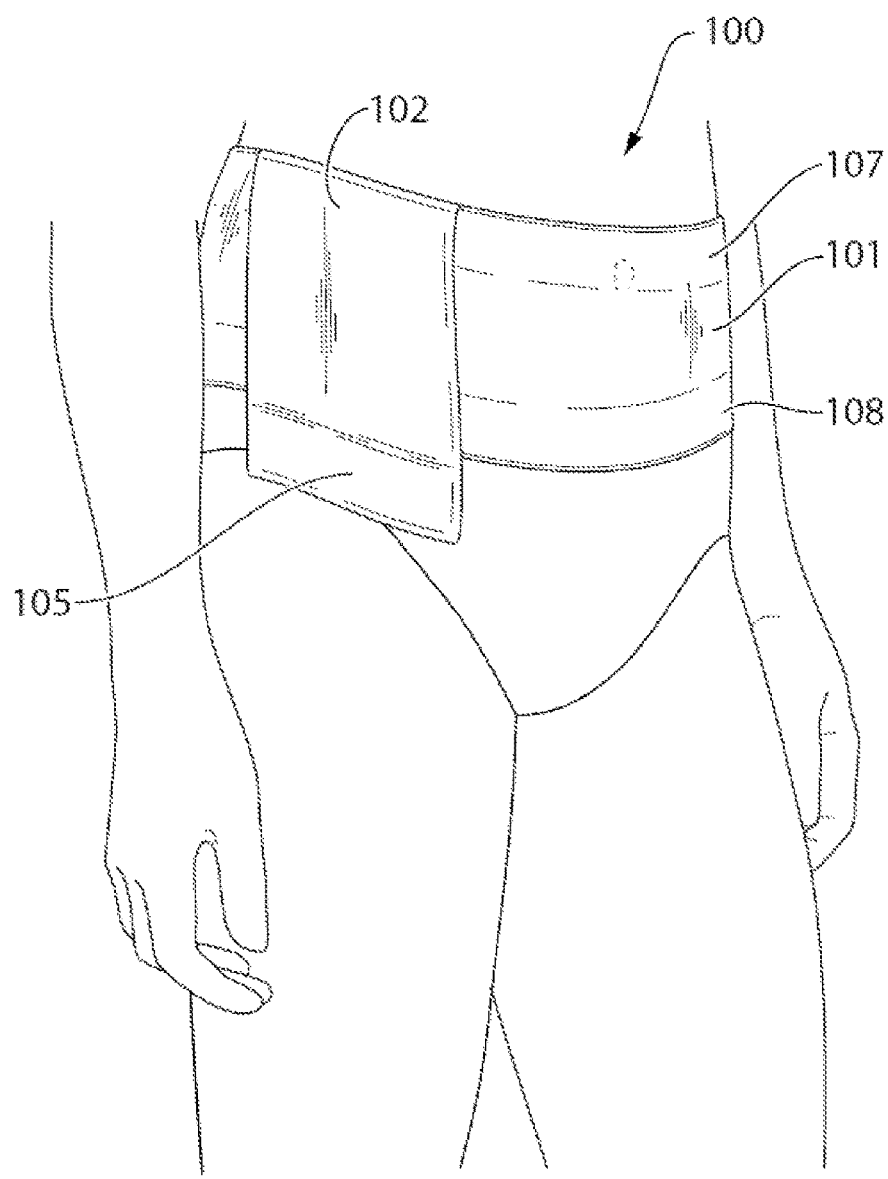
FIG. 1 is a view of an embodiment of the present garment in use.
Figure 2:
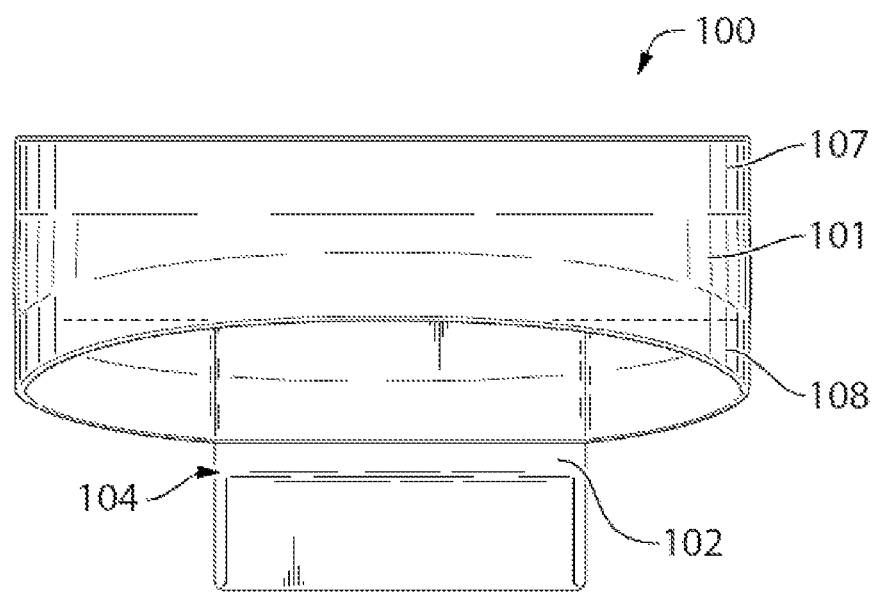
FIG. 2 is a rear view of an embodiment of the present garment.
Figure 3:
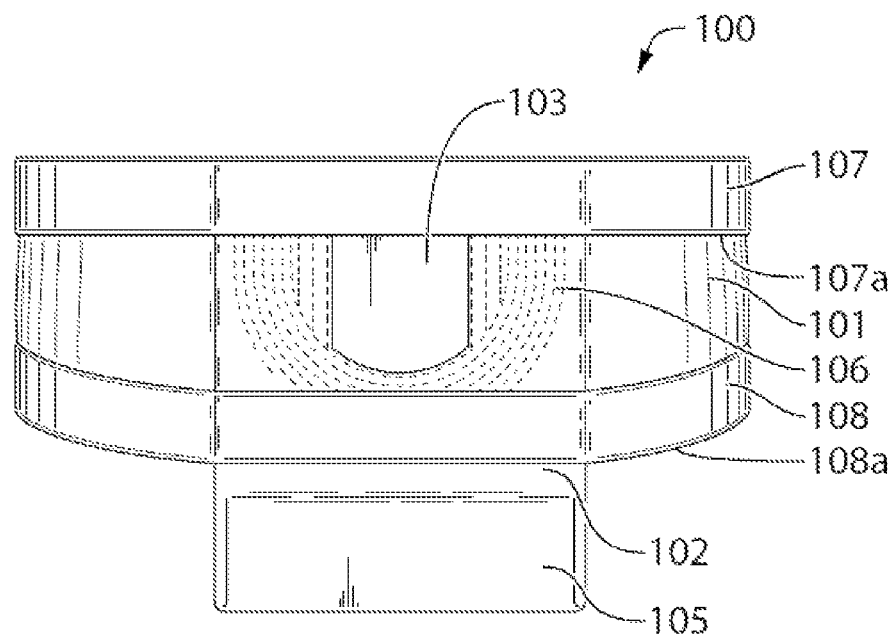
FIG. 3 is a view of the front interior of an embodiment of the present garment.
Figure 4:
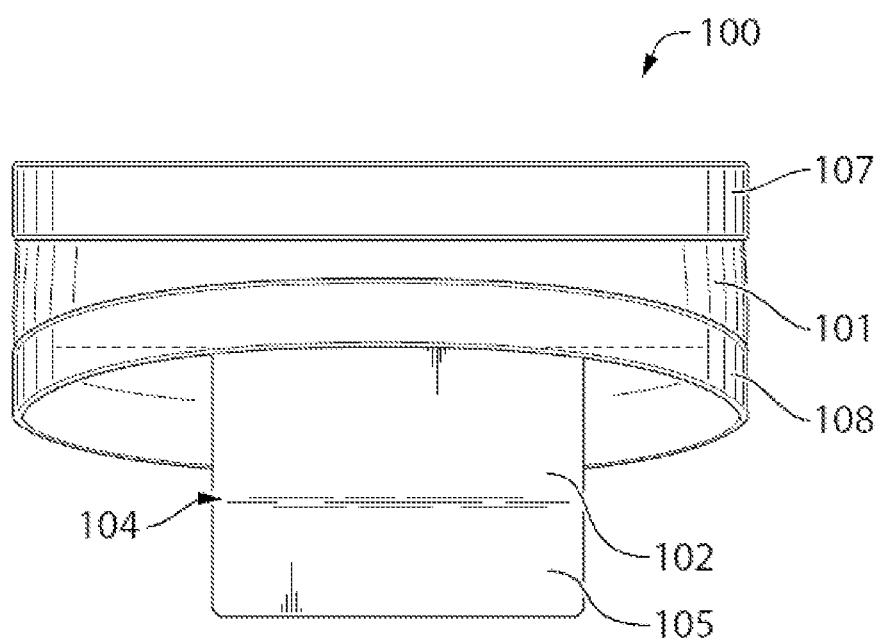
FIG. 4 is a view of the rear interior of an embodiment of the present garment.

Directional terms such as "upper", "lower", "bottom", "top", "right" and "left" are used in the following description for the purpose of providing relative reference only, and are not intended to limit the embodiments of the present invention in any way. The plural and singular forms may be used interchangeably without limitation to the embodiments of the present invention in any way. Embodiments of the present disclosure described herein relate to an ostomy garment.

Referring to FIGS. 1 to 5 and according to an embodiment of the disclosure, there is a garment 100 for accommodating an ostomy pouch. Garment 100 may be constructed primarily of a fabric 101. Any suitable fabric may be used herein. Fabrics may be made from natural, semi-synthetic or synthetic fibres, or a mixture thereof. Natural fibres include silks, cottons, linens, wools, and the like. Semi-synthetic or synthetic fabrics include rayons, microfibers, nylons, polyesters, acrylics, and the like. Preferred fabrics for use in the present garments include, but are not limited to, moisture-wicking fabrics such as nylon Spandex® fabrics. For example, fabric 101 may be a fabric that wicks away moisture such as 4-way stretch "Dri-Tek" performance fabric. Garment 100 comprises a pocket 102 having a first opening 103 for inserting an ostomy pouch (not shown) therethrough and into pocket 102, wherein the first opening 103 faces towards a user of the garment when the garment is worn. Pocket 102 provides a barrier between the ostomy pouch and a user's skin, and may enlarge as the ostomy pouch fills. Pocket 102 optionally comprises a second opening 104 located at the bottom of pocket 102 to enable the user to empty the contents of the ostomy pouch without having to remove the ostomy pouch from pocket 102 or remove garment 100. To provide additional support to the ostomy pouch as it fills, the bottom of the ostomy pouch may be tucked into a secondary pocket 105 disposed within pocket 102. Second opening 104 may be fastened shut by one or more fasteners (such as a clip, zipper, buttons, or the like), and opened at a desired time such as when the user is ready to empty the contents of the ostomy pouch. Certain drainable pouches and urostomy pouches have a closure clamp/lock'n roll system or drain tab that can makes the upper leg sore and irritated from rubbing. Secondary pocket 105 can prevent the bottom of the pouch from hanging free and rubbing against upper leg.

In embodiments of the present disclosure, a fabric 106 surrounds first opening 103. First opening 103 may be of any suitable size for accommodating the ostomy pouch. Fabric 106 may be constructed of the same material as fabric 101. Alternatively, fabric 106 may be constructed of a different material from fabric 101. Preferably, fabric 106 is constructed of a stiffer material (e.g. "Dri-Tek Powernet" 4-way stretch wicking material) than fabric 101. Fabric 106 may be reinforced such as, for example, by stitching. Reinforcing or otherwise stiffening fabric 106 can help provide a secure, stronger sense of pouch to skin contact and, as the pouch fills, can aid in maintaining a more pleasing aesthetic. Fabric 106 surrounding first opening 103 may be reinforced by a plurality of stitching. As depicted in FIG. 1, fabric 106 surrounding a "U" shaped opening 103 is reinforced by a plurality of lines of stitches (e.g. concentric stitches)

wherein some of the stitches form the semi-circular section of the "U" while others form the arms of the "U". First opening 103 may be of any suitable size for accommodating the ostomy pouch such as, for example, "C" shaped, "V" shaped, or the like. Reinforcing stitches may be provided to fabric 106 depending on the shape of first opening 103. In certain embodiments, the user may be guided by the stitch lines to adapt the size of first opening 103 by removing fabric 106 to better fit the size of first opening 103 to the size of the flange ring.

As depicted in the Figures, bands 107 and 108 encircle around edges 100a and 100b respectively of garment 100. At least one, preferably both, of bands 107 and 108 can exert a compressive force on pocket 102. For example, when pocket 102 contains a filled or partially filled ostomy pouch the band or bands exert a compressive force. The present bands help maintain the ostomy pouch close to the user's body thus helping keep a more visually pleasing aesthetic. The bands may be constructed of any suitable material such as, for example, an elastic material. While only two bands are depicted in the Figures, any suitable number of bands may be included. As depicted in the Figures, band 107 may overlap with the top of first opening 103 and band 108 may be tangential to the bottom of first opening 103. As such, at least a portion of first opening 103 may be disposed between edge 107b and edge 108a of bands 107 and 108 respectively. As depicted in the Figures, bands 107 and 108 may be parallel to each other over the width of fabric 106. However, the bands may be oriented relative to one another in any suitable manner. Band 108 and band 107 may converge at the rear of the garment which may help reduce shifting of garment 100. The convergence between bands 107 and 108 preferably roughly coincides with the back mid-line (e.g. along the spine) of the user. The contoured relationship between bands 107 and 108 may help prevent garment 100 from "rising" up the body of the user.

Figure 5:
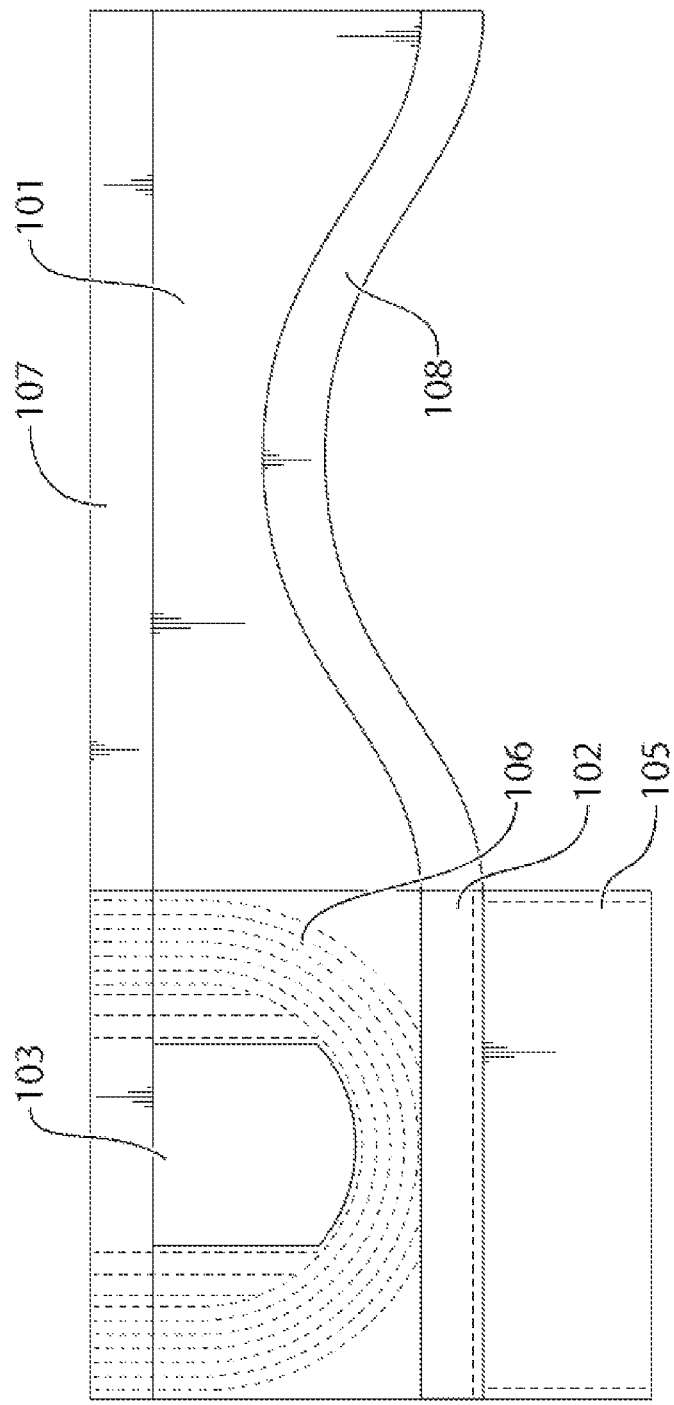
FIG. 5 is a view of a pattern for an embodiment of the present garment.

The present disclosure provides a pattern for a garment comprising garment for accommodating an ostomy pouch, the garment comprising: a pocket for containing the ostomy pouch, the pocket having a first opening that faces a user of the garment when the garment is worn, the first opening for inserting the ostomy pouch therethrough and into the pocket; and two or more bands encircling the garment for exerting a compressive force against the user when the garment is worn; wherein a mid-line along a length of the pocket intersects a mid-line of at least one of the two or more bands. FIG. 5 illustrates a pattern for a garment according to the present disclosure.

In practice, an ostomy pouch may be inserted through first opening 103 into pocket 102. The ostomy pouch may be connected to a flange whose circumferential size is greater than the aperture of first opening 103. That is, the flange may remain on the outside of pocket 102 and first opening 103 and thereby reduce the chance of the ostomy pouch from falling through pocket 102 under the influence of gravity. The flange preferably at least partially overlaps with fabric 106. In one exemplary use of garment 100, the flange also overlaps with one or both of bands 107 and 108 such that the compressive force of the bands press the flange against the skin of the user.

It is contemplated that the different parts of the present description may be combined in any suitable manner. For instance, the present examples, methods, aspects, embodiments or the like may be suitably implemented or combined with any other embodiment, method, example or aspect of the invention.

Unless defined otherwise, all technical and scientific terms used herein have the same meaning as is commonly understood by one of ordinary skill in the art to which this invention belongs. Unless otherwise specified, all patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. Citation of references herein is not to be construed nor considered as an admission that such references are prior art to the present invention.

Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

The invention claimed is:

1. A garment for accommodating an ostomy pouch, the garment comprising:
   (a) a pocket for containing the ostomy pouch, the pocket having a first opening configured to face a user of the garment when the garment is worn, the first opening for inserting the ostomy pouch therethrough and into the pocket;
   (b) a fabric surrounding the first opening of the pocket and wherein the fabric is reinforced by concentric bands of stitching; wherein the fabric is constructed of a stiffer material than the pocket; and
   (c) two or more bands circling the garment and configured to exert a compressive force against the user when the garment is worn;
   wherein a mid-line along a length of the pocket intersects a mid-line of at least one of the two or more bands.

2. The garment as claimed in claim 1, wherein at least one of the two or more bands is elastic.

3. The garment as claimed in claim 1, wherein at least two of the two or more bands are parallel to one another over at least a first portion of the garment.

4. The garment as claimed in claim 1, wherein at least one of the two or more bands converge towards at least another one of the two or more bands over at least a second portion of the garment.

5. The garment as claimed in claim 1, wherein a flange attached to the ostomy pouch overlaps with at least one of the bands, wherein said band exerts a compressive force on the flange when the garment is worn.

6. The garment as claimed in claim 1, wherein the aperture of the first opening is configured to accommodate different ostomy pouch sizes.

7. The garment as claimed in claim 1, wherein the pocket further comprises a second opening configured for emptying the pouch without removing the pouch from the pocket.

8. The garment as claimed in claim 1, further comprising a secondary pocket disposed within the pocket for receiving a portion of the ostomy pouch, wherein the secondary pocket supports a weight of the pouch as the pouch fills.

9. The garment as claimed in claim 1, wherein the first opening is U-shaped.

10. The garment as claimed in claim 1, wherein a flange attached to the ostomy pouch overlaps with two of the two or more bands, wherein said bands exert a compressive force on the flange when the garment is worn.

11. A pattern for manufacturing a garment according to claim 1.

12. A method of manufacturing the garment as claimed in claim 1, the method comprising:
 (b) creating a pocket, the pocket comprising a first face and a second face, the first face comprising a first opening suitable for inserting the ostomy pouch therethrough and into the pocket;
 (b) stitching a fabric surrounding the first opening of the pocket, wherein the fabric is constructed of a stiffer material than the pocket; and
 (c) stitching two or more bands to the first face of the pocket.

13. The method as claimed in claim 12, further comprising reinforcing the first face surrounding the first opening with stitching.

14. The method as claimed in claim 13, wherein the stitching is concentric.

15. The method of as claimed in claim 13, further comprising adapting a size of the first opening by removing fabric from around the first opening along the stitching.

16. The method as claimed in claim 12, further comprising converging at least one of the two or more bands towards at least another one of the two or more bands over a portion of the garment.

* * * * *